United States Patent [19]

Evans et al.

[11] Patent Number: 6,117,859

[45] Date of Patent: *Sep. 12, 2000

[54] METHOD OF RELIEVING CHRONIC INFLAMMATION BY USING 5-ALKYLSULFONYLSALICYLANILIDES

[75] Inventors: Richard T. Evans, East Amherst; Robert A. Coburn, Williamsville; Robert J. Genco, Buffalo; Joseph A. Dunn, Amherst, all of N.Y.

[73] Assignee: The Research Foundation of State University of New York, Amherst, N.Y.

[*] Notice: This patent is subject to a terminal disclaimer.

[21] Appl. No.: 09/407,244

[22] Filed: Sep. 28, 1999

Related U.S. Application Data

[63] Continuation-in-part of application No. 08/963,751, Nov. 4, 1997, Pat. No. 5,958,911.

[51] Int. Cl.⁷ .................................................. A61K 31/63
[52] U.S. Cl. .................................................. 514/166
[58] Field of Search ............................................ 514/166

[56] References Cited

U.S. PATENT DOCUMENTS

| | | | |
|---|---|---|---|
| 4,287,191 | 9/1981 | Coburn et al. | 424/230 |
| 4,358,443 | 11/1982 | Coburn et al. | 514/166 |
| 4,742,083 | 5/1988 | Ritchey | 514/617 |
| 4,939,132 | 7/1990 | Coburn et al. | 514/166 |
| 5,240,696 | 8/1993 | Van Der Ouderaa et al. | 424/49 |

OTHER PUBLICATIONS

Clark et al., J. Med. Chem., 29(1) pp. 25–29 (1986).

*Primary Examiner*—Phyllis G. Spivack
*Attorney, Agent, or Firm*—Hodgson, Russ, Andrews, Woods & Goodyear, LLP

[57] ABSTRACT

A method of treating chronic inflammation in a mammal is disclosed which comprises contacting the affected area with an amount sufficient to ameliorate the inflammatory condition, of a compound of the following formula:

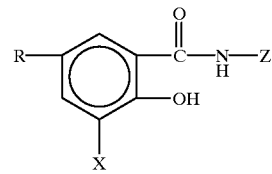

wherein Z is a substituted phenyl ring, R is an alkylsulfonyl group of 1–20 carbon atoms, and X is selected from the group consisting of —CN, —NO$_2$, —H, halogen, lower alkyl and lower haloalkyl.

33 Claims, 1 Drawing Sheet

FIG. 1

METHOD OF RELIEVING CHRONIC INFLAMMATION BY USING 5-ALKYLSULFONYLSALICYLANILIDES

This application is a continuation-in-part of U.S. patent application Ser. No. 08/963,751 filed on Nov. 4, 1997, now U.S. Pat. No. 5,958,911 the disclosure of which is incorporated herein by reference.

FIELD OF INVENTION

This invention relates to the field of anti-inflammatory agents. More particularly, this invention provides a method for the use of 5-alkylsulfonylsalicylanilides in chronic inflammatory conditions.

BACKGROUND OF THE INVENTION

Bacterial infections are often accompanied by inflammation of the infected tissues. For example, during the pathogenesis of periodontal disease, it is generally accepted that while bacteria cause tissue destruction via release of virulence factors, a major role has been proposed for the host itself. The current concept is that the bacteria produce inflammogens including lipopolysaccharides, which trigger mononuclear host cells resulting in bone and connective tissue destruction. These destructive mechanisms include periodontal triggering of macrophage and collagenase which degrades tissue collagen, and stimulation of the production, by mononuclear cells, of interleukin-2 and other cytokines which stimulates local bone resorption.

While antibiotics have been used to treat periodontitis, recent studies show that anti-inflammatory agents also reduce chronic destructive periodontitis (Williams et al., 1989, *J. Periodontology,* 60:485–490; Reddy et al., 1993, *J. Clinical Periodontology* 20:635–640). Most of the anti-inflammatory approaches used so far utilize the systemic non-steroidal anti-inflammatory flurboprofen which has a risk of adverse systemic effects such as gastric ulcers. Furthermore, most anti-inflammatory agents that have been proposed for topical application are designed for systemic use and hence have significant systemic absorption potential, especially when used over long periods of time.

In another inflammatory condition, acne, it is generally accepted that there is increased sebum production in and around sebum producing glands in the skin (Abel et al., 1990, *Scientific Americal Medicine,* 1:212–2110). One of the most frequently occurring severe forms of acne, acne vulgaris, is a chronic disorder of pilosebaceous units primarily on the chest, Ad face, and back, resulting in the formation of large, pus filled lesions accompanied by inflammation of the surrounding tissue.

Many products with different mechanisms of action are currently marketed to treat acne. Quite often the -choice of a particular product depends on the severity of the acne being treated and the side effects that can be associated with the chosen treatment. Some treat acne through the use of antibiotics that kill bacteria and indirectly reduce inflammation. These antibiotics are lipophilic, tending to concentrate in lipid rich sedum and include tetracycline, meclocycline, erythromycin, clindamycin, nadifloxacine. A second family of products use the retinoid class of drugs which function by reducing sebum production. The final class of products are over-the-counter drugs of the keratolytic class which loosen plugs in comedones created by excess sebum and thus rid the skin of dead cells and cell debris. Active ingredients in over-the-counter treatments which perform these functions include benzoyl peroxide, resorcinol, salicylic acid, and sulfur.

Although prescription antibiotics are used for treating severe acne, there are two major problems with their use. First, there has been an increase in bacterial resistance to antibiotics. Second, there is the concern that a prescribed antibiotic can have serious side effects. Currently sold "over-the-counter" formulations that list antibacterial claims are generally effective only at treating mild cases of acne.

Other approaches to treat inflammatory condition include the use of salicylanilides (U.S. Pat. No. 4,742,083) of the general formula:

wherein $R_1$, $R_2$ and $R_3$ are defined hydrocarbon attachments and Y is —OH or a phenolic ester group. These salicylanilide derivatives have also been shown to be effective anti-plaque agents (U.S. Pat. No. 4,287,191 and U.S. Pat. No. 2,358,443). The most effective of these compounds is defined by the formula:

where n=6, X is and —$R_3$ is a meta-trifluoromethylphenyl group (AMCF3-8). This compound has a pKa of 6.1 rendering it relatively insoluble in aqueous solutions at neutral pH.

U.S. Pat. No. 5,2406,696 discloses the use of 2',4,4'-trichloro-2-hydroxy-diphenyl-ether (Triclosan™) as an anti-inflammatory agent against periodontitis.

Thus, currently available topical antiinflammatory compounds have either high systemic absorption or low solubility in formulations typically used in topical applications. A need therefore exists for effective anti-inflammatory compounds, which are also useful in chronic inflammatory condition, that are lipophilic thereby reducing the risk of systemic absorption, and are also easily solubilized in formulations suitable for topical application.

SUMMARY OF THE INVENTION

An object of the present invention is to provide methods for relief of inflammation in mammals.

Another object of the present invention is to provide a method for relief of chronic inflammation, such as acne.

Another object of the present invention is to provide a method which involves the use of lipophilic agents that are minimally absorbed systemically, are effective against inflammation and can be incorporated into suitable topical formulations.

A further objective of the present invention is to provide methods for the topical use of 5-alkylsulfonylsalicylanilide derivatives in the management of inflammation.

DETAILED DESCRIPTION OF THE INVENTION

Definitions

By the term "lower alkyl" as used herein for the purposes of specification and claims is meant an alkyl group of from 1 to 10 carbon atoms.

By the term "partition coefficient" as used herein for the purposes of specification and claims is meant the $\log_{10}P$ where P is the ratio of the molar concentrations of the compositions of the composition in octanol-water system. Partition coefficient is a measure of the lipophilic character of the compound. A partition coefficient of 4 therefore means that the ratio of the concentration of the composition in octanol to the concentration in water is $10^4$ or 10,000 to 1.

By the term "high lipophilicity" as used herein for the purposes of specification and claims is meant a partition coefficient greater than 4.

By the term "substituted" as used herein for the purposes of specification and claims is meant that at least one hydrogen in the compound is replaced with a moiety containing one or more carbon, oxygen, sulfur, nitrogen or halogen atoms.

The present invention provides a method for the use of 5-alkylsulfonylsalicylanilides for the treatment of inflammation. These compounds have previously been shown to have antimicrobial properties especially against the microorganisms associated with dental plaques and associated oral diseases.

The method of the present invention involves the use of highly lipophilic compounds encompassed by the following formula:

wherein Z is a substituted phenyl ring and the substitution on Z consists of replacing at least one hydrogen atom by an electron withdrawing group, wherein R is an alkylsulfonyl group of 1–20 carbon atoms, and X is selected from the group consisting of —CN, —NO₂, —H, halogen, lower alkyl and lower haloalkyl.

Thus, the compounds of the preferred embodiment may be represented by the following formula:

wherein, the substitution on Z is represented by Y and Y is independently at each occurrence, an electron withdrawing group and desirably is not strongly hydrophilic or water solubilizing. Some suitable Y groups are —H, —CF₃, —CN and —NO₂. Preferably, X is —H, and Y is —CF₃ or —CN attached at the meta or para position.

Some examples of specific compounds in accordance with the invention have the formula:

where R is

X is —H and Y is —CF₃ (TMF-6), or —CN (TMC-6) attached at the meta position;
where R is X is —H and Y is —CN (TPC-6) at the para position; where R is X is —H and Y is —CF₃(TMF-7), or —CN(TMC-7) attached at the meta position;
where R is

X is —H and Y is —CN (TPC-7) attached at the para position;

where R is

X is —H and Y is —CF$_3$ (TMF-8), or —CN (TMC-8) attached at the meta position;

where R is

X is —H and Y is —CN (TPC-8) attached at the para position;

where R is

X is —H and Y is —CF$_3$ (TMF-9), or —CN (TMC-9) attached at the meta position;

where R is

X is —H and Y is —CN (TPC-9) attached at the para position;

where R is

X is —H and Y is —CF$_3$ (TMF-10), or —CN (TMC-10) attached at the meta position;

where R is

X is —H and Y is —CN (TPC-10) attached at the para position;

where R is

X is —H and Y is —CF$_3$ (TMF-12), attached at the meta position;
where R is X is —H and Y is —CF$_3$ (TMF-14) attached at the meta position.

The compounds of the present invention can be synthesized according to the method disclosed in U.S. Pat. No. 4,939,132, which method is hereby incorporated by reference. Briefly, the compounds are synthesized by reacting a salicylic acid with a chlorosulfonic acid to form a 5-chlorosulfonylsalicylic acid. The 5-chlorosulfonylsalicylic acid is then reacted with an alkali metal sulfite to form 5-sulfinylsalicylic acid which is then reacted with an appropriate alkyl halide to produce the 5-alkylsulfonylsalicylic acid.

An advantage of the compounds of the present invention is that they have unexpectedly higher potency than the salicylanilide derivatives disclosed as anti-inflammatory agents in the prior art (U.S. Pat. No. 4,742,083). In the compounds of the present invention, the 5-alkyl groups are connected to the salicylanilides via a sulfonyl group whereas, in the compounds disclosed in U.S. Pat. No. 4,742,083, the 5-alkyl or 5-acyl groups are connected to the salicylanilides either directly or through The introduction of the sulfonyl group at the 5-position surprisingly confers a significantly higher potency to the compounds of the present invention. Since these compounds are highly lipophilic, they are insoluble in H$_2$O. However, and quite unexpectedly, these compounds were found to be soluble in aqueous solutions of both anionic and non-ionic detergents at concentrations routinely used in topical applications. This property of these compounds makes them suitable for topical formulations with a low risk of systemic uptake because of their high lipophilicity.

The compounds of this invention may be incorporated into formulations for topical application. Such applications include, but are not limited to, topical formulations for mouth, skin, scalp, ear, nose, eyes, vagina and rectum. The inflammation treated by these compounds includes various disorders including gingivitis, acne, arthritis, rosacea, eye inflammation including conjunctivitis, and inflammatory bowel diseases including Crohn's disease. The compounds of this invention may also be used in topical formulations for veterinary use for the relief of inflammation in various conditions including gingivitis, conjunctivitis and arthritis. The formulations can be applied to, without limitation, mouth, skin, scalp, ear, nose, eyes, vagina and rectum.

The method in accordance with the present invention for the relief of inflammation comprises contacting the affected area with the compounds of this invention in a pharmaceutically acceptable carrier containing nonionic or ionic detergent. Such a carrier base may be selected from the group consisting of petroleum jelly, lanolin, paraffin wax, alkanols and mixtures thereof. By using a base such as lanolin or petroleum jelly, a spreadable formulation is obtained and by using a base such as paraffin wax, a stick for topical application is obtained. In addition, the compounds of this invention may also be incorporated into liquid carriers containing non-ionic or ionic detergents. The non-ionic detergent, Tween 80™ and the anionic detergent, sodium lauryl sulfate (SLS) may be used.

The above compounds can be used for the relief of inflammation in mammals, particularly humans, by topical application of formulations containing the compounds of the present invention. These compounds can be used, without limitation, in tooth pastes, mouth rinses, soaps, shampoos, skin ointments, skin lotions, eye ointments, eye drops, ear drops, and nasal drops.

The following examples illustrate the invention.

EXAMPLE 1

The solubility of representative compounds of this invention in various solvent systems was determined. The solvents included ethanol, propylene glycol, SLS, Tween 80™ and combinations thereof.

12, is more lipophilic than AMCF3-8 of U.S. Pat. No. 4,742,083, and at the same time displays a greater solubility than AMCF3-8 in the anionic and nonionic surfactant solutions. As will be clear from Example 4 of this invention, TMF-12 is also more potent than AMCF3-8. As a result, even the most active compounds of this invention can be formulated at useful concentrations in simple systems compatible with mammalian usage including human usage. The surfactants useful for solubilizing the compounds of this invention are routine additives in many topical formulation like tooth pastes and mouth rinses.

EXAMPLE 2

An analytical method to determine concentration and stability of some representative compounds of this invention in solution employing high pressure liquid chromatography (HPLC) was developed and validated. Both isocratic and gradient mobile phases of acetonitrile, water and methanol were investigated on a C-18 silica reverse solid phase column (Zorbax). Results were obtained using a 12 minute gradient of 80% to 100% methanol/water at a flow rate of 1.5 ml/minutes. Detection was carried out by measuring absorbance at 280 nm. Under these conditions TMF-10 and TMC-l0 each produced symmetrical peaks with retention times of 7.5 and 3.0 minutes, respectively. TMF-8 and TMF-12 had retention times of 4 and 9 minutes respectively.

| Solvent System | Salifluor | TPC-10 | TMC-10 | TMF-10 | TMF-12 |
|---|---|---|---|---|---|
| Ethanol @ 19° C. | 13.04 | 11.5 | 36.7 | 44.67 | 13.59 (22° C.) |
| Propylene Glycol @ 20° C. | 0.55 | 0.81 | 1.94 | 1.7 | 6.66 |
| pH 10 K-buffer @ 35° C. | $1.14 \times 10^{-3}$ | $3.45 \times 10^{-3}$ | $5.58 \times 10^{-3}$ | $<1 \times 10^{-4}$ | — |
| pH 10 Na-buffer @ 22° C. | $3.91 \times 10^{-3}$ | $9.16 \times 10^{-3}$ | $7.2 \times 10^{-3}$ | $1.89 \times 10^{-3}$ | $<1 \times 10^{-4}$ |
| +0.5% SLS | — | 0.3 | 3.13 | 0.37 | 1.28 |
| +1% SLS | 0.23 | 0.69 | 4.27 | 0.92 | 1.66 |
| +2% SLS | 0.29 | 0.91 | 6.68 | 1.28 | 2.93 |
| +4% SLS | 0.38 | 1.81 | 7.9 | 2.08 | 5.74 |
| +0.5% Tween 80 ™ | — | — | 0.77 | 0.76 | 1.34 |
| +1.5% Tween 80 ™ | — | — | 2.24 | 2.02 | 4.29 |
| +3.0% Tween 80 ™ | — | — | 4.69 | 4.13 | 8.34 |
| +2% SLS + 0.5% Tween 80 ™ | — | — | 3.98 | 1.35 | 3.54 |
| +2% SLS + 1.0% Tween 80 ™ | — | — | 4.74 | 1.91 | 4.01 |
| +2% SLS + 2.0% Tween 80 ™ | — | — | 5.05 | 2.87 | 5.86 |

The data exemplify a number of conclusions regarding the effect of structural variation on the physical properties of these agents. Although soluble to the extent of 1–4% in ethanol, they are insoluble in water unless ionized. The $pK_a$ of these compounds is about 5.2. As anions they have limited aqueous solubility, 0.0001–0.001% with slightly better solubility as sodium salts. However, both anionic detergents e.g., SLS and non-ionic detergents e.g., Tween 80™ increase aqueous solubility to the 0.1% –0.8% range. Thus, even though the compounds of this invention are highly lipophilic, surprisingly, a 2% SLS solution can solubilize these hydrophobic compounds to useful concentration of 0.1% to 0.3% without the presence of any organic co-solvent, possibly due to more efficient micellar incorporation. The most potent compound of this invention, TMF- Each compound had a linear relationship between concentration injected and area under the curve with correlation coefficients no less than 0.99. The lowest detectable quantity measured for all three compounds was 5.0 ng.

EXAMPLE 3

A 0.3 mg/ml solution of TMF-10 in 30% ethanolic water was maintained at 40° C. for several weeks. At various times samples were analyzed for decomposition employing the HPLC method described in Example 2. Following four weeks under these conditions, no decomposition of TMF-10 was detected.

EXAMPLE 4

The anti-inflammatory effect of selected compounds of this invention were compared to those of Triclosan™ and hydrocortisone in a modified 12-tetradecanoyl 13-phorbol acetate (TPA) mouse ear inflammation assay. TPA was used as an inflammogen rather than croton oil because TPA gives a well characterized inflammatory response at very low concentrations. The use of this mouse model has been shown to reflect the clinical parameters characteristic of inflammatory responses in humans and predictive of the effectiveness of therapeutic agents in patients (see for example, Kimura et al., 1995, *Biological and Pharmaceutical Bull.* 18:1617–1619; Rao et al., *J. Lipid Mediators & Cell Signaling* 10:213–228; Fretland et al., *Inflammation* 19:333–346). This model can therefore be used to study the pharmacokinetics, clinical efficacy and adverse side effects of anti-inflammatory agents. To quantitate inflammation, ear punches from treated animals were used to measure increased ear mass (edema) and myeloperoxidase (MPO) activity. For the inhibition studies, ear biopsies were weighed six hours after treatment with TPA and the simultaneous application of the compound of the present invention. All the compounds were diluted in acetone. Following this, the biopsies were frozen and subsequently used to measure inhibition of MPO activity, an estimate of polymorphonuclear (PMN) lymphocyte activity in the affected area. Percent inhibition of edema was calculated as [c-t]/c x 100, where c and t are increases in ear weight in control and treated mice, respectively.

Initially a dose-response curve for TPA-induced mouse ear edema was generated in order to determine the concentration of TPA to be employed in the inhibition studies. TPA produced a theoretical dose-response curve for edema with an $ED_{50}$ of 80 ng/ear and an $ED_{90}$ of 200 ng/ear in two separate experiments. $ED_{50}$ is the dose at which 50% of the maximum effect was observed while $ED_{90}$ is the dose at which 90% of the maximum effect was observed. TMF-12, which is representative of all the compounds tested in this study, inhibited TPA induced mouse ear edema in a dose-dependent fashion. The $ED_{50}$ values for the compounds tested are as follows:

| Compound | $ED_{50}$ (mg/20 ul) | $ED_{90}$ (mg/20 ml) |
|---|---|---|
| TMF-8 | 36.1 | 273.2 |
| TMF-10 | 31.9 | 225.1 |
| TMF-12 | 15.3 | 121.6 |
| TPC-10 | 64.3 | 548.6 |
| TMC-10 | 72.6 | 615.5 |
| Salifluor | 155.9 | 1241.8 |
| Triclosan ™ | 133.9 | 832.2 |

Each of the compounds of this invention was more potent than Salifluor (AMCF3-8), which is the most potent compound disclosed in U.S. Pat. No. 4,742,083. TMF-12 was the most potent of all, ten times more potent than Salifluor. The compounds of this invention are also more potent than Triclosana. Hydrocortisone, a steroid, was the most potent anti-inflammatory agent tested.

EXAMPLE 5

As a confirmation of the anti-inflammatory activity and in an attempt to further define the mechanism of inhibition produced by the alkylsulfonylsalicylanilides, MPO activity was measured in representative ear biopsies. The enzyme was extracted from the tissue by using a combination of homogenization in the presence of a detergent, freezing and thawing, and sonication. The change in absorbance was measured with time using o-dianisidine and $H_2O_2$ as the substrate in an automated plate reader. As shown below, TPA-induced increase in MPO was inhibited in TMF-12 treated ears at a dose approximately 10-fold less than that which inhibited edema.

| TMF-12 (mg/20 ml) | MPO Activity (D OD/min) |
|---|---|
| 0 | 624.9 |
| 0.8 | 590.2 |
| 1.24 | 327.3 |
| 8 | 56.5 |
| 12.4 | 54.8 |
| 80 | 27.6 |
| 124 | 21 |

This implies that one of the mechanisms through which the alkylsulfonylsalicylanilides inhibited inflammation is via inhibition of the PMN pathway, preventing macrophage infiltration and release of autacoids such as histamine, nitric oxide, arachidonic acid and peroxides.

EXAMPLE 6

This embodiment demonstrates that the compounds of the present invention are effective in treating chronic inflammatory conditions. The acute skin inflammation model described in Example 1, tests the ability of a compound to prevent inflammation and thus must be applied prophylactically. Most clinical situations, however, are present as chronic inflammatory conditions. A useful and well accepted model has evolved that permits the evaluation of agents for treating chronic inflammatory conditions involves multiple applications of the phorbol ester TPA to mouse ears which induces a prolonged chronic inflammatory like response characterized by edema, cell infiltration and epidermal hyperplasia Stanley et a., 1991, *Skin Pharmacol,* 4:262–271. The effects of the compounds of the present invention and Salifluor on chronically inflamed skin was measured in the mouse ear model that utilizes multiple TPA doses over a 10-day period to produce the inflammatory response. The compounds were tested in a single vehicle, acetone and compared with Salifluor and Triclosan, which have been reported to have anti-inflammatory activity in clinical trials.

The assay used female CD-1 mice (7–9 weeks of age). Following a 2-week quarantine, mice were randomly assigned to test groups (5 mice/groups). TPA (10 uL of 0.01 TPA in acetone) was administered to both the inner and outer surface of each ear (2μg/ear) on day 0,2,4,7, and 9 on protocol. On Day 7,8 and 9, two applications of test article were applied to each ear 2 and 4 hours after dosing with TPA. The test articles were administered in 10 uL aliquots to both the inner and outer surface of each ear (20 μl total/dose). The candidate drugs were tested at several different concentrations (e.g., 5, 1.25, and 0.125 mg/ear) to determine a maximum effective dose within a range that could be effectively applied. Hydrocortisone-17-valerate (HCV, 20μg/ear) was employed as a positive control. Mice were sacrificed at Day 10 on protocol and uniform punch biopsies (approximately 8 mm dia.) were taken from each ear. While on protocol, dermal irritation was scored semiquantitatively at Day 1,3,5,8, and 10.

Inhibition of TPA stimulated increased ear weight was used as an initial measure of efficacy for all of the agents tested. One biopsy from each mouse was also quick frozen and stored at −70° C. for later assay of myleoperoxidase, an enzyme associated with infiltrating PMN, or other measure of efficacy. The remaining biopsy from each mouse treated with Trifluorosal or HCV was fixed in formalin and processed for histopathologic evaluation, including measurement of cellular infiltration (PMNs, endothelial cells, macrophages) and epidermal thickness at 20 random sites along the length of the specimen.

Initially, a dose-response curve for multiple doses of TPA to produce mouse ear weight gain was generated in order to determine the concentration of TPA to be employed in the inhibition studies. TPA produced a maximal response for ear weight gain under these conditions at 2μg/ear, with marginal effects below 1μg/ear. This is an unexpected result in view of the results for a single concentration of TPA to cause acute ear weight gain (measured after 6 hours exposure and attributed to localized edema and PMN infiltration) which produced a calculated $ED_{50}$ of 80 ng/ear, and $ED_{90}$ of 200 ng/ear (n=2 separate experiments). Another major difference between the multiple TPA dose (or chronic assay for inflammation) and the single TPA dose (or acute assay for inflammation) in the mouse ear is sensitivity to Non-steroidal antiinflammatory drugs (NSAIDs) and antihistamines. The chronic assay is insensitive to NSAIDs, including the more potent compounds such as diclofenac and piroxicam, and to antihistamines; whereas the acute assay is inhibited by fairly weak NSAIDs, such as Naproxen and Ibuprofen, and is inhibited by common antihistamines (231). As disclosed in Example 1, in the acute assay, all of the 5-(n-alkylsulfonyl)salicylanilide compounds evaluated inhibited TPA induced mouse ear edema and PMNB associated myleoperoxidase activity in a dose-dependent fashion with $ID_{50}$ values below 100 μg/ear. Trifluorosal was the most potent 5-(n-alkylsulfonyl)salicylanilide in this assay with $ID_{50}$ edema=18 μg/ear and $ID_{50}$ myleoperoxidase —1.8 mg/ear. Also in the acute assay, a clear structure-activity relationship among the alkylsalicylanilides for inhibition of edema was demonstrated. All of the novel 5-(n-alkylsulfonyl)salicylanilides tested were more potent than Salifluor (A8-F) or Triclosan (Table 1). Hydrocortisone (20μg/ear) was the most potent anti-inflammatory agent tested.

Five separate experiments to evaluate the potency of each test compound in the chronic inflammation assay using inhibition of ear weight gain as a biological readout were conducted. The first experiment validated the assay with regard to effect to Hydrocortisone 17-valerate (86% inhibition at 20μg/ear), however, only Trifluorosal showed any degree of inhibition (28% at 500μg/ear) over the dose range used (5–500 ag/ear). In the remaining experiments a higher dose range of each test compound was employed (1.25–5 mg/ear). At these concentrations only TMF-10 and Trifluorosal demonstrated consistent activity. The maximum inhibition produced by Trifluorosal was 34.4% at 5.0 mc/ear, but lower concentrations of Trifluorosal (2.5 and 1.25 mg/ear) gave 27.3 and 37.5% inhibition, respectively, indicating that the compound had reached a plateau in effect in the delivery vehicle used (acetone). TMF-10 produced 69.8 and 0.0% inhibition at 5.0, 2.5, and 1.25 mg/ear, respectively. Table 4 shows a comparison of all of the agents tested at the 1.25 mg/ear level.

TABLE 4

% Inhibition of Ear Weight Gain Produced by Multiple doses of TPA in Mice

| Compound | Actual | 1% Inhibition (1.25 eg/ear) Relative to Hydrocortisone (HCV) = 100% |
|---|---|---|
| TMF-8 | 0 | 0 |
| TMF-10 | 54.7 | 59.9[a] |
| TMF-12 | 37.3 | 61.8[b] |
| TMC-10 | 0 | 0 |
| TPC-10 | 0 | 0 |
| AB-F (Salifluor) | 0 | 0 |

[a]Assay #2, 20 μg HCV/ear produced 107% decrease in weight to TPA treated biopsies
[b]Assay #1, 20 μg HCV/ear produced a 71% decrease in weight of TPA treated biopsies The histopathological analysis of the ear biopsies for mice treated with multiple doses of TPA to produce chronic inflammation may be more informative that total ear weight, and in this case showed very interesting and unexpected results. As expected, treatment with TPA produced a dramatic hyperplasia of the epidermis as well as inflammatory changes in the dermis. The more relevant changes in the dermis include hyperemia (increase in the amount of blood in blood vessels) and an apparent increase in the number of the cellularity in the dermis. Surprisingly, the predominant cells were not PMN but rather a combination of different cell types including endothelial cells, fibroblasts, macrophages, PMNs, and mast cells. There were no clear signs of edema and there were no clear indications of an increase of the thickness of the dermis. Thus, increase of weight in the biopsies of TPA treated animals seemed to be mainly contributed by the hyperplasia of the epidermis and may be secondarily contributed by an increase of density of the dermis, but not an increase of the size of the dermal compartment.

Figure 1:
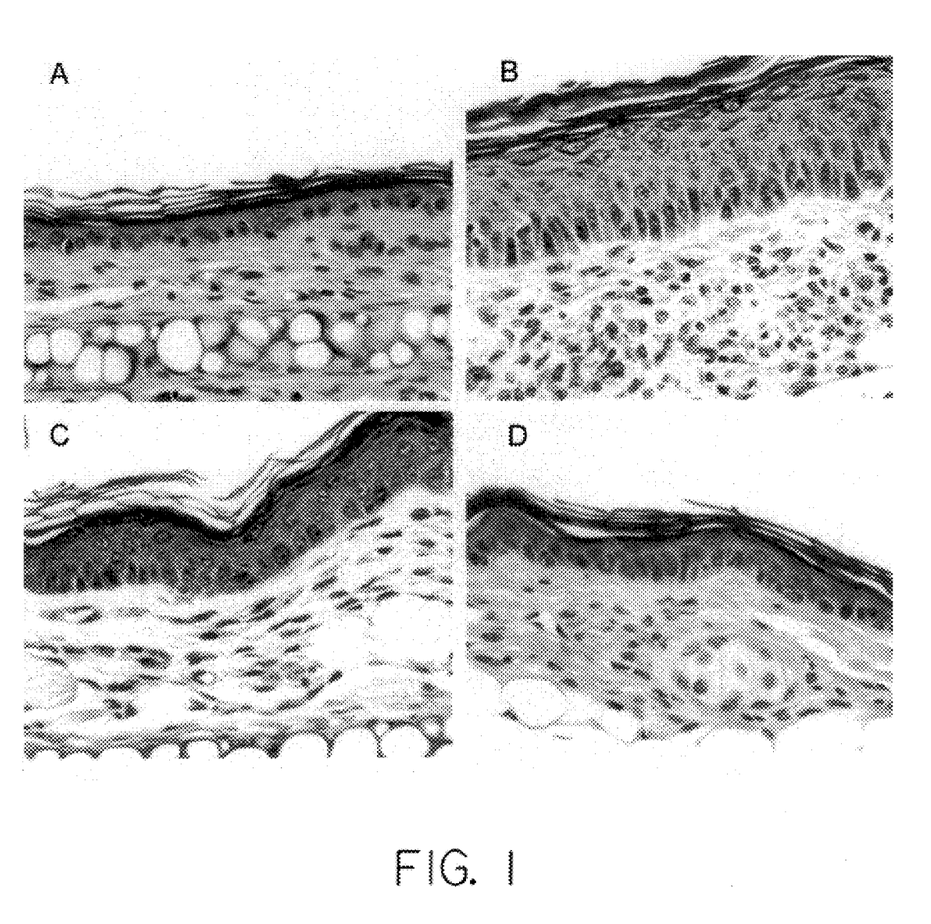
FIG. 1 is a photomicrograph of a representative vertical section from mouse ear for (A)—acetone control; (B)—TPA treated; (C)—TPA and Trifluorosal (1.25 mg/ear) treated and (D)—hydrocortisone 17-valerate (0.02 mg/ear) treated.

Both Triflurosal and hydrocortisone reduced the epidermal thickness as well as the cellularity of the dermis (FIG. 1). Blood vessels were not as prominent in the samples of animals treated with the compounds and the histopathological analysis suggests that both blood vessel dilation and angiogenesis may have been inhibited by the test articles.

Control epidermis treated with each of the test articles did not show signs of toxicity at the microscopic levels and the ear plugs of these samples did not appear different from the samples of the control (untreated) or vehicle (acetone) treated animals.

In order to confirm the subjective observations, quantitative determinations of 3 parameters (epidermal thickness, dermal thickness, and dermal cellularity) in the skin of negative controls (acetone), positive controls (TPA), and TPA treated skin treated with 3 doses of test article (Trifluorosal) and hydrocortisone were carried out. Epidermal thickness reflects the reactive proliferative activity induced by TPA in the dermis: dermal thickness reflects primarily Ad edema but may also be affected by other phenomena, such as formation of granulation tissue, collagen synthesis, the activity of myofibroblasts, etc. Cellularity of the dermis is frequently used as a surrogate marker of inflammatory changes in the dermis. In the case of acute inflammation, PMNs better reflect those changes but in these samples the subjective information indicated that PMNs were a minor component of the cellularity of the dermis and therefore it was concluded that the number of total cells in the dermis would better reflect the dermal changes.

Determination of the epidermal thickness was performed under the microscope with a calibrated scale placed in the eyepiece. Ten determinations were carried out in the epidermis covering the outside of the ear using a 40× objective and a 10× eyepiece (400× total). The measurements were taken from the basal side of the basal layer (basement membrane) to the outer side of the last nucleated cell of the dermis. The average of the 10 measurements expressed in microns was entered in the table.

Determination of dermal thickness was performed using a similar technique. To avoid variability caused by the difference in sizes between the base and tip of the ear, only 3 measurements were performed in the center of the sample. The measurements were performed from the basement membrane of the external and internal epithelial and therefore include, in addition to both dermis (external and internal), the cartilage. The cartilage represents less than 10% of the thickness of the ear and does not appear profound changes in the treated and untreated animals.

Cellularity of the dermis was calculated by projecting a calibrated grid into the dermis and counting cells in the known area of the dermis. Areas of hair follicles or sebaceous glands were avoided. Five fields were counted and the results were adjusted to the number of cells in 1,000 square microns.

The results of individual animals were entered in the table and the averages and standard deviation were calculated using an EXCEL database. In addition, the results were also expressed as a percentage of the control (acetone treated). Furthermore, the percentage of inhibition of the test articles were calculated using the following formula:

$$\text{Percentage of inhibition} = \frac{(1 - \text{Test article value} - \text{Acetone value})}{\text{TPA value} - \text{Acetone value}} \times 100.$$

As can be observed in Table 5, the quantitative measurements confirm the original subjective observations. Epidermal thickness and the cellularity of the dermis correlate well with the observed changes in weight as previously observed. In contrast, the thickness of the epidermis appears not to reflect these changes.

TABLE 5

Inhibition of Increased Epidermal Thickness and Dermal Cellularity in Mice Produced by Multiple doses of TPA following treatment with trifluorosal of HCV

| Compound | Dose (mg/ear) | % Inhibition Epidermal Thickness | % Inhibition Dermal Cellularity |
|---|---|---|---|
| TMF-12 | 5.00 | 30.0 | 47.6 |
|  | 2.50 | 11.4 | 64.3 |
|  | 1.25 | 48.0 | 24.6 |
| Hydrocortisone | 0.02 | 58.6 | 78.6 |

EXAMPLE 7

To test for tolerance of the administered compounds, male weaning Sprague-Dawley rats were fed in a single dose of 2.5 or 0.75 g/kg of TMF-12, TMF-10, TMC-10 or TPC-10 in 5% carboxymethyl cellulose (CMC) or CMC alone. The animals (6–7 rats per group) were observed for 7 days for morbidity or mortality. At completion of the 7 day observation period, necropsies were performed on all animals. No statistical weight differences were noted between the control group (sham treated) and the experimental drug treated groups, indicating that there was no loss of appetite due to the drug. All animals doubled their weight during the seven day experimental period. No illness or deaths occurred during the seven day period. No observable gross pathology attributable to the drugs was seen at necropsy.

From the foregoing, it will be obvious to those skilled in the art that various modifications in the above-described methods can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, and all changes which come within the meaning and range of equivalency of the claims are therefore, intended to be embraced therein.

What is claimed is:

1. A method of treating chronic inflammation in a mammal, which comprises contacting the affected area with an amount sufficient to ameliorate the inflammatory condition, of a compound of the following formula:

in a pharmaceutically acceptable carrier, said carrier comprising a detergent, where Z is a substituted phenyl ring, wherein the substitution on Z is selected from the group consisting of —CF$_3$, —CN and —NO$_2$, wherein R is an alkylsulfonyl group of 1 to 20 carbon atoms, and X is selected from the group consisting of —CN, —NO$_2$, —H, halogen, lower alkyl and lower haloalkyl.

2. The method of claim 1, wherein said compound has a partition coefficient greater than 4 and the substituted moieties in the phenyl ring Z group have a combined overall electron withdrawing effect on the phenyl ring of the Z group.

3. The method of claim 1, wherein the compound is and Y is independently at each occurrence an electron withdrawing group.

4. The method of claim 3, wherein Y is selected from the group consisting of —CF$_3$, —CN and —NO$_2$.

5. The method of claim 1, wherein the compound has the formula

15

X is —H and Y is selected from the group consisting of —CF$_3$ and —CN.

6. The method of claim 5, wherein R is

Y is —CF$_3$ attached at the meta position.

7. The method of claim 5, wherein R is and Y is —CN attached at the meta position.

8. The method of claim 5, wherein R is and Y is —CN attached at the para position.

9. The method of claim 5, wherein R is and Y is —CF$_3$ attached at the meta position.

10. The method of claim 5, wherein R is and Y is —CN attached at the meta position.

11. The method of claim 5, wherein R is and Y is —CN attached at the para position.

16

12. The method of claim 5, wherein R is and Y is —CF$_3$ attached at the meta position.

13. The method of claim 5, wherein R is and Y is —CN attached at the meta position.

14. The method of claim 5, wherein R is and Y is —CN attached at the para position.

15. The method of claim 5, wherein R is and Y is —CF$_3$ attached at the meta position.

16. The method of claim 5, wherein R is and Y is —CN attached at the meta position.

17. The method of claim 5, wherein R is and Y is —CN attached at the para position.

18. The method of claim 5, wherein R is and Y is —CF$_3$ attached at the meta position.

19. The method of claim 5, wherein R is and Y is —CN attached at the meta position.

20. The method of claim 5, wherein R is and Y is —CN attached at the para position.

21. The method of claim 5, wherein R is and Y is —$CF_3$ attached at the meta position.

22. The method of claim 5, wherein R is and Y is —$CF_3$ attached at the meta position.

23. The method of claim 1, wherein the pharmaceutically acceptable carrier comprises a material selected from the group consisting of petroleum jelly, lanolin, paraffin wax, alkanols and mixtures therefor.

24. The method of claim 1, wherein the pharmaceutically acceptable carrier is a liquid.

25. The method of claim 1, wherein said detergent is selected from the group consisting of nonionic detergent, anionic detergent and mixtures thereof.

26. The method of claim 25, wherein the non ionic detergent is Tween-80™.

27. The method of claim 26, wherein the concentration of Tween-80™ in the pharmaceutically acceptable carrier is from about 0.5 percent to about 3 percent.

28. The method of claim 25, wherein the anionic detergent is sodium lauryl sulfate.

29. The method of claim 28, wherein the concentration of sodium lauryl sulfate is from about 0.5 percent to about 4 percent.

30. The method af claim 25, wherein the concentration of the compound in the pharmaceutically acceptable carrier is between about 0.1 percent to about 1.0 percent.

31. The method of claim 30, wherein the concentration of the compound in the pharmaceutically acceptable carrier is about 0.1 percent to about 0.3 percent.

32. The method of claim 1, wherein the mammal is a human being.

33. The method of claim 1, wherein the mammal is an animal.

* * * * *

UNITED STATES PATENT AND TRADEMARK OFFICE
CERTIFICATE OF CORRECTION

PATENT NO.    : 6,117,859
DATED         : September 12, 2000
INVENTOR(S)   : Evans et al.

It is certified that error appears in the above-identified patent and that said Letters Patent is hereby corrected as shown below:

Column 1,
Line 4, insert:
-- This invention was made with Government support under Grant No. 2R42DE11618 awarded by the National Institutes of Health. The Government has certain rights in the invention. --

Signed and Sealed this

Seventh Day of October, 2003

JAMES E. ROGAN
*Director of the United States Patent and Trademark Office*